United States Patent [19]

Lindsey

[11] Patent Number: 4,629,819

[45] Date of Patent: Dec. 16, 1986

[54] NOVEL HYBRID CORN PLANT
[75] Inventor: Marvin F. Lindsey, Boone, Iowa
[73] Assignee: DeKalb-Pfizer Genetics, DeKalb, Ill.
[21] Appl. No.: 727,632
[22] Filed: Apr. 26, 1985
[51] Int. Cl.$^4$ .............................................. A01H 1/02
[52] U.S. Cl. ......................................................... 800/1
[58] Field of Search ........................................ 47/58, 1

Primary Examiner—Robert E. Bagwill
Attorney, Agent, or Firm—Sughrue, Mion, Zinn, Macpeak, and Seas

[57] ABSTRACT $F_1$ hybrid corn plants DK 524, seeds produced by cultivation of the hybrid, and plant cells which upon growth and differentiation produce the novel hybrid.

3 Claims, No Drawings

NOVEL HYBRID CORN PLANT

FIELD OF THE INVENTION

This invention relates generally to the production of maize commonly known in the United States as corn and more particularly concerns the development and production of inbred and hybrid maize with certain desired characteristics.

BACKGROUND OF THE INVENTION

Commercial hybrid maize generally grows from about 7 to 9 feet tall with each plant having either one or two ears. The ear normally grows about one-third the way up the plant or about 2½ to 3½ feet from the ground. Consequently, the maize plant, while providing a large ear has a substantial leaf and stalk structure and a considerable mechanical stability problem in that the heavy ear is about 3 feet from the ground with 6 feet of stalk and the tassels extend above that. In the past, efforts have been made to develop strong stalk and branching of secondary roots in maize to help alleviate this stability problem. While these efforts have improved the mechanical stability of maize considerably, heavy wind storms and rain can still wreak havoc in a field of maize.

While great gains have been made in the use of hybrid maize in productivity and yield per acre, over that of maize varieties, further major and immediate substantial gains due to hybrid vigor are not anticipated. Consequently, efforts must be directed to improving the characteristics of the commercial hybrid maize plant by genetic or environmental manipulation.

Hence, one of the objects of this invention is to significantly increase the yield per acre of maize. For example, in the Apr. 17, 1974 edition of *The Wall Street Journal*, the article entitled "In Search of Superbean", it was pointed out that soybeans could not easily be hybridized and, therefore, fell far behind corn in productivity increase. During the period of 1950 to 1973, soybeans increased in productivity from 21.8 to 27.8 bushels per acre while corn increased from 38.4 to 91.4 bushels per acre.

Other advantageous characteristics can also be sought by the methods of plant breeding and genetic manipulation. For example, excellent plant seedling vigor is advantageous are as germination, early stand and stay green characteristics. The present invention provides a novel corn hybrid with all of these advantages and other advantageous characteristics as well.

SUMMARY OF THE INVENTION

The present invention comprises novel $F_1$ generation hybrid corn plants designated DK 524. Seeds of this hybrid have been deposited with American Type Culture Collection, 12301 Parklawn Drive, Rockville, Md. 20852, and have received accession number ATCC 40180. This invention further comprises novel hybrid corn DK 524 and the novel seeds produced by the cultivation of novel hybrid DK 524 corn plant. Cells which upon growth and differentiation produce novel hybrid corn plants DK 524 also form a part of this invention.

DETAILED DESCRIPTION OF THE INVENTION

As the female parent used to produce the novel corn hybrid plants and seeds of the present invention, a proprietary inbred line, 78010 developed by DeKalb Pfizer Genetics was employed. A proprietary inbred line 78060A, also developed by DeKalb-Pfizer Genetics was employed as the male parent.

The two parental inbred lines, 78010 and 78060A, were planted in pollinating proximity of each other. They can be planted in alternating rows, in blocks or in any convenient planting pattern. The plants of both inbred ilnes were allowed to grow unmolested until time of flowering. They can be thinned at about the 3-leaf stage if required and will also preferably be treated with fertilizer and/or other agricultural chemicals as considered appropriate by the seed grower. At the time of flowering, the tassels were removed from all plants of the female parent inbred line, 78010. This was accomplished by hand but can be done by machine as desired. Alternatively, chemical sterilization on conversion of the female parent by addition of a cytoplasmic male sterile trait can be used. Both inbred lines were then allowed to continue to grow and natural cross-pollination occurred by the action of wind as is normal in grasses including corn. Of course, only pollen from the male parent inbred line, 78060A, was available for pollination, the tassels, or pollen bearing flowering parts, having been removed from all plants of female inbred line 78010. In this regard, the fields where the hybrid seeds of this invention were produced were well isolated from other corn fields to prevent any accidental contamination with ambient pollen. Such isolation techniques are normal in the seed corn industry and are well known to those skilled in the art.

Both parent inbred lines of corn were allowed to continue to grow but the ears from the female parent inbred line, 78010, only were harvested to obtain the novel $F_1$ hybrid corn seeds, DK 524, of the present invention. The male parent inbred line ears can be harvested, if desired, but they will not be useful as hybrid seed corn.

To obtain the novel $F_1$ hybrid corn plants of the present invention, the seeds thus produced were planted at the next proper growing season. All parts of such plants of hybrid DK 524 are claimed as part of the present invention including roots, stems, leaves and all flowering parts including pollen grains. The cells of plants of hybrid DK 524 which can be grown in culture and differentiated or regenerated to form plants also constitute a part of this invention. For details of generation procedures, see C. E. Green and C. A. Rhodes, "Plant Regeneration In Tissue Culture of Maize", 1982, *Maize for Biological Research*, ed. W. F. Sheridan, Plant Molecular Biology Association, Charlottesville, Virginia, pages 367–372.

Furthermore, the seeds produced by $F_1$ hybrid DK 524 plants on maturity also form a part of the present invention. The novel $F_1$ hybrid corn seeds, DK 524, were planted and the resulting hybrid plants were grown to maturity, the ears being harvested mechanically by normal means. Various measurements were made on the hybrid plants and on the seeds they produced and these results are shown in comparison with DeKalb-Pfizer Genetics commercial hybrid, T1000, and in comparison with Pioneer Hi-Bred International commercial hybrid P3732, each of which has a similar harvest moisture level and is thus a fair subject for comparison.

TABLE 1

| Hybrid | Yield (Bushels/Acre) | Harvest Moisture (%) | Seedling Vigor (%) | Early Stand (%) | Plant Height (Inches) | Ear Height (Inches) | Not Barren (%) | Stay Green (%) | Not Stalk Lodged (%) | Not Root Lodged (%) |
|---|---|---|---|---|---|---|---|---|---|---|
| DK 524 | 137.4 | 23.0 | 112.3 | 104.2 | 91.2 | 44.5 | 100.9 | 96.3 | 99.5 | 97.8 |
| T 1000 | 121.2** | 23.3* | 102.2** | 105.0 | 78.9** | 34.6** | 99.6** | 85.9** | 100.1 | 98.9 |
| DK 524 | 136.5 | 22.9 | 111.8 | 104.4 | 87.7 | 42.3 | 100.9 | 99.2 | 99.7 | 97.5 |
| PIONEER 3732 | 128.0** | 22.8 | 110.8 | 106.7** | 81.1** | 39.0** | 100.5 | 99.7 | 103.6** | 99.0* |

*statistically significant at the 5% level.
**statistically significant at the 1% level.
NOTE: With the exception of Harvest Moisture in Table 1 above, all (%) values are expressed relative to the mean of experiments in which these hybrid comparisons were made.

An examination of Table 1 reveals that novel hybrid DK 524 has advantageous characteristics in comparison with or in comparison to the similar and commercially successful hybrid T1000. The novel variety of this invention is superior in the important characteristics of yield, seedling vigor, early stand, and stay green characteristics. The advantages have come about in a most unexpected and surprising way from the cross between the above disclosed parent varieties.

In addition to the characteristics shown in Table 1, the following characteristics of DK 524 were also observed.

Emergence
  (1–9, 1=Best)—2
Vigor
  (1–9, 1=Best)—5
Stalk
  Height (cm)—251
  Ear Height (cm)—131
  Anthocyanin—Slight
  Tillers—Few
  Brace Roots—Some
Leaves
  Angle—Intermediate
  Number—19.6
Leaf Sheath
  Anthocyanin—Present
  Pubesence—Very
Tassel
  Length (cm)—42.2
  Branching—Some
  Branch Angle—Intermediate
  Anther Color—Yellow
Ear
  Silk Color—Yellow
  Husk Bracts—Short
  Ear Per Stalk—1.2
  Length (cm)—19.6
  Shape—Cylindrical
  Diameter (cm)—5.1
  Kernel Rows—15.8
  Shank Length (cm)—13.9
  Husk Number—8.5
  Husk Length (cm)—22.6
  Husk Width (cm)—11.6
  Cob Color—Red
  Cob Diameter (cm)—2.5
Kernel
  Type—Dent
  Color
    A. Cap—Lemon-Yellow
    B. Sides—Orange
  Form-Elongated
50% Pollen Shed
  Days—78
  Degree Days—1322
50% Silk
  Days—77
  Degree Days (GDU)—1306
  Shank Diameter (cm)—1.1
  Glume Color—Green-Yellow
  Glume Band—Present
  Tassel Attitude—Intermediate
  Brace Root Color—Green This disclosure is illustrative and the present invention is defined in the appended claims.

While the invention has been described in detail and with reference to specific embodiments thereof, it will be apparent to one skilled in the art that changes and modifications can be made without departing from the spirit and scope of the invention.

I claim:
1. $F_1$ generation hybrid corn plant DK 524.
2. Seed produced by the cultivation of the hybrid corn plant of claim 1.
3. A plant cell which upon growth and differentiation produces the hybrid corn plant of claim 1.

* * * * *